United States Patent [19]

Teutsch et al.

[11] Patent Number: 4,515,787

[45] Date of Patent: May 7, 1985

[54] STEROIDS

[75] Inventors: Jean G. Teutsch, Pantin; Roger Deraedt, Pavillons-sous-Bois; Josette Benzoni, Livry Gargan, all of France

[73] Assignee: Roussel Uclaf, Paris, France

[21] Appl. No.: 532,739

[22] Filed: Sep. 15, 1983

[30] Foreign Application Priority Data

Oct. 5, 1982 [FR] France .................................. 82 16668

[51] Int. Cl.³ .......................... C07J 5/00; A61K 31/56
[52] U.S. Cl. .................................. 514/180; 260/397.45
[58] Field of Search .............................. 424/238, 243; 260/397.45

[56] References Cited

U.S. PATENT DOCUMENTS 4,353,899 10/1982 Teutsch et al. ...................... 424/243

Primary Examiner—Elbert L. Roberts
Attorney, Agent, or Firm—Charles A. Muserlian

[57] ABSTRACT

Novel 9α,11β-dichloro-16α-methyl-$\Delta^{1,4}$-pregnadiene 3,20-diones of the formula

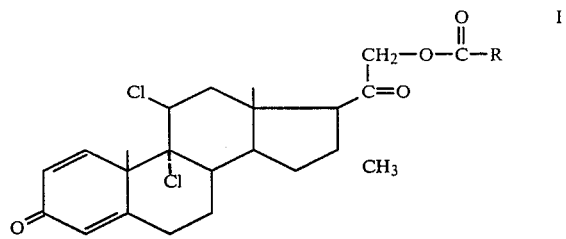

wherein R is selected from the group consisting of trimethylsilylphenyl, cyclododecyloxy, dicyclopentylmethoxy and cyclohexylmethoxy having a suprising "in loco" anti-inflammatory activity limited to place of inflammation without systemic effects and a process for their preparation.

18 Claims, No Drawings

STEROIDS

STATE OF THE ART

French Pat. No. 2,342,738 describes and claims compounds of the formula

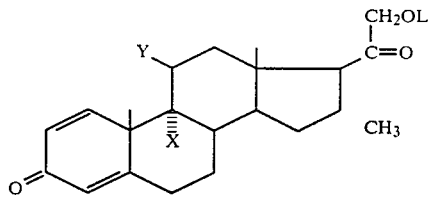

wherein L is hydrogen or an acyl of an organic carboxylic acid of 1 to 18 carbon atoms and Y is a 11β-chloro and X is 9α-chloro or 9α-bromo or Y is 11β-fluoro and X is 9α-chloro. It's French patent of addition No. 2,381,065 describes and claims 9α,11β-dichloro-16α-methyl-$\Delta^{1,4}$-pregnadiene-21-ol-3,20-dione. French Pat. No. 2,462,443 and U.S. Pat. No. 4,353,899 describe 9α,11β-dichloro-16α-methyl-21-oxycarbonyl dicyclohexylmethoxy-$\Delta^{1,4}$-pregnadiene-3,20-dione. Also pertinent is U.S. Pat. No. 3,329,570.

OBJECTS OF THE INVENTION

It is an object of the invention to provide the novel $\Delta^{1,4}$-pregnadiene-3,20-diones of formula I and a novel process for their preparation.

It is another object of the invention to provide novel "in loco" anti-inflammatory compositions and to a novel method of treating inflammation in warm-blooded animals.

These and other objects and advantages of the invention will become obvious from the following detailed description.

THE INVENTION

The novel compounds of the invention are 9α,11β-dichloro-16α-methyl-$\Delta^{1,4}$-pregnadiene-3,20-diones of the formula

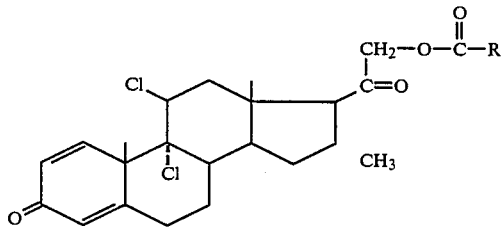

wherein R is selected from the group consisting of trimethylsilylphenyl, cyclododecyloxy, dicyclopentylmethoxy and cyclohexylmethoxy.

Among the preferred compounds of formula I are those wherein R is trimethylsilylphenyl or cyclododecyloxy and especially 9α,11β-dichloro-16α-methyl-21-[(3-trimethylsilylphenyl)-carbonyloxy]-$\Delta^{1,4}$-pregnadiene-3,20-dione.

The process of the invention for the preparation of the compounds of formula I comprises reacting 9α,11β-dichloro-16α-methyl-$\Delta^{1,4}$-prepgnadiene-21-ol-3,20-dione with an acid halide of the formula

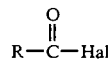

wherein Hal is a halogen and R has the above definition. Hal is preferably chlorine or bromine and the reaction is effected in the presence of a basic agent such as pyridine or collidine.

In a preferred mode of the process, 9α,11β-dichloro-16α-methyl-$\Delta^{1,4}$-pregnadiene-21-ol-3,20-dione is reacted with 3-trimethylsilyl-benzoic acid chloride in the presence of an amine base to form 9α,11β-dichloro-16α-methyl-21-[(3-trimethylsilylphenyl)-carbonyloxy]-$\Delta^{1,4}$-pregnadiene-3,20-dione.

The "in loco" anti-inflammatory compositions of the invention are comprised of an anti-inflammatorily effective amount of at least one compound of formula I and a pharmaceutical excipient. The compositions may be in the form of aerosols, powders, pommades, creams, gels, enemas or colic disintegratable tablets.

Examples of suitable excipients are aqueous and non-aqueous vehicles, fatty bodies of animal or vegetable origin, paraffin derivatives, alcohols such as glycols, diverse wetting agents, dispensants or emulsifiers, preservatives, talc and lactose.

The compositions of the invention are inactive when orally administered and are administered topically to the skin or mucous and are devoid of systemic effects of the cortisonic type. Preferably, the compositions are administered in the form of an aerosol.

The compositions are therapeutically useful against asthma, against edemas, dermatosis, pruritsis, diverse forms of eczema, solar erythema, local inflammation such as colitis.

While the compounds of the invention fall within the scope of the compounds described in French Pat. No. 2,342,738 and No. 2,462,443, tests have clearly shown the differences in "in loco" anti-inflammatory activity as presented infra.

Among the preferred compositions of the invention are those wherein R is 3-trimethylsilylphenyl or cyclododecyloxy.

The novel method of the invention for combatting inflammation in warm-blooded animals comprises topically applying to warm-blooded animals an anti-inflammatorily effective amount of at least one compound of formula I. Preferably, the compounds of Example 1 are applied in aerosol form by spraying 1 to 6 times per day at a rate of 0.1 to 2 mg of the active compound per spray.

In the following examples there are described several preferred embodiments to illustrate the invention. However, it should be understood that the invention is not intended to be limited to the specific embodiments.

EXAMPLE 1

9α,11β-dichloro-16α-methyl-21-[(3-trimethylsilylphenyl)-carbonyloxy]-$\Delta^{1,4}$-pregnadiene-3,20-dione STEP A: 3-trimethylsilyl-benzoic acid chloride Carbon dioxide was bubbled through 15 ml of a solution of 0.9M of 3-trimethylsilylphenyl magnesium bromide in tetrahydrofuran until the exothermic reaction ceased and the mixture was poured into water. The mixture was made alkaline by addition of 2N sodium hydroxide solution and was extracted with ether. The organic phase was dried over anhydrous magnesium sulfate and was evaporated to dryness under reduced pressure. The residue was dissolved in 5 ml of thionyl chloride and the solution was held at room temperature for 2 hours and was evaporated to dryness under reduced pressure. The residue was taken up three times in anhydrous benzene and the benzene phase was evaporated to obtain 3-trimethylsilylbenzoic acid chloride which was used as is for the next step.

STEP B:

$9\alpha,11\beta$-dichloro-$16\alpha$-methyl-21-[(3-trimethylsilylphenyl)-carbonyloxy]-$\Delta^{1,4}$-pregnadiene-3,20-dione 600 mg of $9\alpha,11\beta$-dichloro-$16\alpha$-methyl-$\Delta^{1,4}$-pregnadiene-21-ol-3,20-dione were added with stirring to a mixture of 5 ml of pyridine and the product of Step A in an ice bath and the mixture was poured into an aqueous sodium bicarbonate solution. The mixture was extracted with ether and the organic phase was washed with 2N hydrochloric acid, dried and evaporated to dryness under reduced pressure. The residue was chromatographed over silica gel and was eluted with a 9-1 benzene-ethyl acetate mixture to obtain 520 mg of $9\alpha,11\beta$-dichloro-$16\alpha$-methyl-21-[(3-trimethylsilylphenyl)-carbonyloxy]-$\Delta^{1,4}$-pregadiene-3,20-dione which was crystallized from methanol.

Analysis: $C_{31}H_{28}CL_2O_4Si$ Calculated: %C 64.91, %H 6.68, %Cl 12.36, Found: %C 65.3, %H 6.8, %Cl 12.6.

EXAMPLE 2

$9\alpha,11\beta$-dichloro-$16\alpha$-methyl-21-[(cyclododecyloxy)-carbonyloxy]-$\Delta^{1,4}$-pregnadiene-3,20-dione A solution of 4.3 g of cyclododecanyl chloroformate in 8 ml of dioxane was added with stirring under nitrogen over 90 minutes to a solution of 2 g of $9\alpha,11\beta$-dichloro-$16\alpha$-methyl-$\Delta^{4,9}$-pregnadiene-21-ol-3,20-dione, 4 ml of pyridine and 8 ml of dioxane and the mixture was stirred at room temperature for 16 hours and was poured into 200 ml of iced water. The mixture was extracted with ethyl acetate and then with chloroform and the organic phases were separately washed with 0.1N hydrochloric acid. Then the combined phases were dried and evaporated to dryness under reduced pressure. The residue was chromatographed over 125 g of silica gel and was eluted with a 94-6 chloroform-ethyl acetate mixture to obtain 2.51 g of $9\alpha,11\beta$-dichloro-$16\alpha$-methyl-21-[(cyclododecyloxy)-carbonyloxy]-$\Delta^{1,4}$-pregnadiene-3,20-dione and 120 g of impure product.

The 2.51 g of the said product were empasted with hot ethanol and the temperature was returned to room temperature. The mixture was iced and vacuum filtered and the product was dried for 16 hours at 70° C. at a pressure of 0.5 mm Hg to obtain 2.418 g of the desired product.

Analysis: $C_{35}H_{50}Cl_2O_5$ Calculated: %C 67.52, %H 8.11, %Cl 11.41, Found: %C 67.5, %H 8.1, %Cl 11.5.

EXAMPLE 3

$9\alpha,11\beta$-dichloro-$16\alpha$-methyl-21-[(dicyclopentylmethoxy)-carbonyloxy]-$\Delta^{1,4}$-pregnadiene-3,20-dione STEP A: dicyclopentylmethanol 12 ml of ethyl formate were added dropwise under nitrogen at room temperature to 450 ml of a solution of 0.7M of cyclopentyl magnesium bromide in tetrahydrofuran and the mixture was stirred at room temperature for 60 hours and was poured into aqueous saturated ammonium chloride solution. The mixture was extracted with ether and the organic phase was dried and evaporated to dryness at 40° C. under reduced pressure. The residue was distilled to obtain 11 g of cyclopentylmethanol with a boiling point of 35° C. at 0.3 mm Hg. The residual product was distilled under reduced pressure to obtain 8.3 g of product with a boiling point of 100° C. at 0.4 mm Hg.

STEP B: Dicyclopentylmethanol chloroformate 2.7 g of N,N-dimethyl-aniline were added to 31 ml of a solution of 0.13 g/ml of phosgene in benzene and a solution of 3.1 g of the product of Step A in 6 ml of benzene was added dropwise with stirring to the mixture. The mixture was stirred at room temperature for 42 hours and was cooled in an ice bath. The mixture was acidified by addition of 12 ml of N hydrochloric acid and the decanted organic phase was washed with water, dried and evaporated to dryness under reduced pressure to obtain 7.5 g of residue. 5.5 g of the residue was distilled under reduced pressure to obtain 2 g of dicyclopentylmethanol chloroformate with a boiling point of 135° C. at 1 mm Hg and a Rf=0.68 (9:1 chloroform-ethyl acetate eluant).

STEP C:

$9\alpha,11\beta$-dichloro-$16\alpha$-methyl-21-[dicyclopentylmethoxy)-carbonyloxy]-$\Delta^{1,4}$-pregnadiene-3,20-dione A solution of 2 ml of dicyclopentylmethanol chloroformate in 4 ml of dioxane was added with stirring at room temperature over two hours to a solution of 1 g of $9\alpha,11\beta$-dichloro-$16\alpha$-methyl-$\Delta^{1,4}$-pregnadiene-21-ol-3,20-dione, 2 ml of pyridine and 4 ml of dioxane and the mixture was stirred at room temperature for 4 hours and was poured into an ice-water mixture. The mixture was extracted with ether and the organic phase was washed with 0.1N hydrochloric acid, dried and evaporated to dryness. The residue was chromatographed over silica gel to obtain 1.387 g of product which after crystallization from absolute ethanol yielded $9\alpha,11\beta$-dichloro-$16\alpha$-methyl-21-[(dicyclopentylmethoxy)-carbonyloxy]-$\Delta^{1,4}$-pregnadiene-3,20-dione melting at 170° C.

Analysis: $C_{34}H_{46}Cl_2O_5$ Calculated: %C 67.42, %H 7.66, %Cl 11.71, Found: %C 67.5, %H 7.7, %Cl 11.7.

EXAMPLE 4

$9\alpha,11\beta$-dichloro-$16\alpha$-methyl-21-[(cyclohexylmethoxy)-carbonyloxy]-$\Delta^{1,4}$pregnadiene-3,20-dione A solution of 2.1 g of hexahydrobenzyl chloroformate in 4 ml of dioxane was added over 2 hours at room temperature to a solution of 1 g of $9\alpha,11\beta$-dichloro-$16\alpha$-methyl-$\Delta^{1,4}$-pregnadiene-21-ol-3,20-dione, 2 ml of pyridine and 4 ml of dioxane and the mixture was stirred at room temperature and was poured into 100 ml of iced water. The mixture was extracted with ether and the organic phase was washed with 0.1N hydrochloric acid, dried and evaporated to dryness under reduced pressure. The residue was chromatographed over silica gel and was eluted with a 92-8 chloroform-ethyl acetate mixture. The product was crystallized from absolute ethanol to obtain 1.054 g of $9\alpha,11\beta$-dichloro-$16\alpha$-methyl-21-[(cyclohexylmethyoxy)-carbonyloxy]-$\Delta^{1,4}$-pregnadiene-3,20-dione melting at 150° C.

Analysis: $C_{30}H_{40}Cl_2O_5$ Calculated: %C 65.33, %H 7.31, %Cl 12.86, Found: %C 65.0, %H 7.3, %Cl 10.0.

EXAMPLE 5

An aerosol preparation was prepared dispensing a dose of 0.5 mg of the product of Example 1, 0.15 mg of emulsifier and 50 mg of propellant.

PHARMACOLOGICAL DATA

In the following tests, the compounds of the invention were compared with dexamethasone and 9α,11β-dichloro-16α-methyl-21-acetoxy-Δ$^{1,4}$-pregnadiene-3,20-dione [product X] described in French Pat. No. 2,342,738, 9α,11β-dichloro-16α-methyl-21-pentanoyloxy-Δ$^{1,4}$-pregnadiene-3,20-dione [product Y] described in French Pat. No. 2,381,065 and 9α,11β-dichloro-16α-methyl-21-oxycarbonyldicyclohexylmethoxy-Δ$^{1,4}$-pregnadiene-3,20-dione [product Z] described in French Pat. No. 2,462,443.

A. "in loco" anti-inflammatory activity

Conventional female Wistar rats weighing 100 to 110 g received an implantation under the skin of the thorax 2 cotton pellets containing the test compound prepared by wetting the cotton pellets with 20 μl of ethanol containing the test compound and drying the pellets for 24 hours at 40° C. The activity is expressed in mg of compound per pellet. The animals were killed on the morning of the third day of the test and the pellets surrounded by granuloma tissue were weighed fresh and after being dried at 60° C. for 18 hours. The granuloma weight was determined by subtracting the weight of the cotton pellet.

The thymus was removed and weighed to evaluate the systemic thymolytic activity of the products and the results of Table I are expressed as DA$_{50}$ per pellet or a dose which provoked a 50% granuloma inhibition and a 50% thymus involution.

TABLE I

| Product | DA$_{50}$ in mg | |
|---|---|---|
|  | Granuloma test | Thymus test |
| Example 1 | 0.0004 | inactive at 1 |
| Example 2 | 0.0005 | >1 |
| X | 0.012 | 0.360 |
| Y | >0.1 | >0.1 |
| Z | 0.0008 | inactive at 0.8 |
| Dexamethasone | 0.4 | 0.015 |

The results of the granuloma test show that the compounds of Examples 1 and 2 have a superior "in loco" activity than product X,Y and Z and dexamethasone and that the product of Example 1 presents a much less systemic effect than the prior art products, particularly dexamethasone.

B. Oral anti-inflammatory activity

The classical granuloma test used was that modified by Meier et al [Experientia, Vol. 6 (1950), p. 469] using conventional female Wistar rats weighing 100 to 110 g. The rats each received an implantation of a 10 mg cotton pellet under the thorax skin and the rats then received orally the test compound twice a day for two days. 16 hours after the last administration, the animals were killed and the pellets by granuloma tissue were weighed fresh and after drying at 60° C. for 18 hours. The granuloma tissue weight was determined by substracting the pellet weight.

At the same time, the thymus was weighed to determine the thymolytic activity of the products and DA$_{50}$ or the dose which provided a 50% inhibition of granuloma and a 50% involutions of the thymus is reported in Table II.

TABLE II

| Product | DA$_{50}$ mg/kg | |
|---|---|---|
|  | Granuloma test | Thymus test |
| Example 2 | inactive at 50 | inactive at 50 |
| X | >100 | 50 |
| Y | >50 | 15 |
| Z | >80 | >80 |
| dexmethasone | 0.05 | 0.035 |

The compound of Example 2 is only very slightly ative orally as compared to dexamethasone.

Various modifications of the products and processes of the invention may be made without departing from the spirit or scope thereof and A is to be understood that the invention is intended to be limited only as defineed in the appended claims.

What we claim is:

1. A 9α,11β-dichloro-16α-methyl-Δ$^{1,4}$-pregnadiene-3,20-dione of the formula

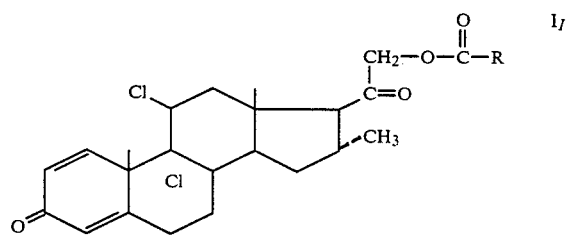

wherein R is selected from the group consisting of trimethylsilylphenyl, cyclododecyloxy, dicyclopentylmethoxy and cyclohexylmethoxy.

2. A compound of claim 1 wherein R is selected from the group consisting of trimethylsilylphenyl and cyclododecyloxy.

3. A compound of claim 1 which is 9α,11β-dichloro-16α-methyl-21-[(3-trimethylsilylphenyl)-carbonyloxy]-Δ$^{1,4}$-pregnadiene-3,20-dione.

4. A compound of claim 1 which is 9α,11β-dichloro-16α-methyl-21-[(cyclododecyloxy)-carbonyloxy]-Δ$^{1,4}$-pregnadiene-3,20-dione.

5. A compound of claim 1 which is 9α,11β-dichloro-16α-methyl-21-[(dicyclopentylmethoxy)-carbonyloxy]-Δ$^{1,4}$-pregnadiene-3,20-dione.

6. A compound of claim 1 which is 9α,11β-dichloro-16α-methyl-21-[(cyclohexylmethoxy)-carbonyloxy]-Δ$^{1,4}$-pregnadiene-3,20-dione.

7. An "in loco" anti-inflammatory composition devoid of systemic corticocoid effects comprising an anti-inflammatorily effective amount of at least one compound of claim 1 and a pharmaceutical excipient.

8. A composition of claim 7 wherein R is trimethylsilylphenyl or cyclododecyloxy.

9. A composition of claim 7 wherein the active compound is 9α,11β-dichloro-16α-methyl-21-[(3-trimethylsilylphenyl)-carbonyloxy]-Δ$^{1,4}$-pregnadiene-3,20-dione.

10. A composition of claim 7 wherein the active compound is 9α,11β-dichloro-16α-methyl-21-[(cyclododecyloxy)-carbonyloxy]-Δ$^{1,4}$-pregnadiene-3,20-dione.

11. A composition of claim 7 wherein the active compound is 9α,11β-dichloro-16α-methyl-21-[(dicyclopentylmethoxy)-carbonyloxy]-Δ$^{1,4}$-pregnadiene-3,20-dione.

12. A composition of claim 7 wherein the active compound is 9α,11β-dichloro-16α-methyl-21-[(cyclohexylmethoxy)-carbonyloxy]-Δ$^{1,4}$-pregnadiene-3,20-dione.

13. A method of treating inflammation in warm-blooded animals comprising topically applying to warm-blooded animals an anti-inflammatorily effective amount of at least one compound of claim 1.

14. A method of claim 13 wherein R is trimethylsilylphenyl or cyclododecyloxy.

15. A method of claim 13 wherein the active compound is 9α,11β-dichloro-16α-methyl-21-[(3-trimethylsilylphenyl)-carbonyloxy]-Δ$^{1,4}$-pregnadiene-3,20-dione.

16. A method of claim 13 wherein the active compound is 9α,11β-dichloro-16α-methyl-21-[(cyclododecyloxy)carbonyloxy]-Δ$^{1,4}$-pregnadiene-3,20-dione.

17. A method of claim 13 wherein the active compound is 9α,11β-dichloro-16α-methyl-21-[(dicyclopentylmethoxy)-carbonyloxy]-Δ$^{1,4}$-pregnadiene-3,20-dione.

18. A method of claim 13 wherein the active compound is 9α,11β-dichloro-16α-methyl-21-[(cyclohexylmethoxy)-carbonyloxy]-Δ$^{1,4}$-pregnadiene-3,20-dione.

* * * * *